(12) United States Patent
Yamada (10) Patent No.: US 9,997,449 B2
(45) Date of Patent: Jun. 12, 2018

(54) SEMICONDUCTOR DEVICE CONNECTION STRUCTURE, ULTRASONIC MODULE, AND ULTRASONIC ENDOSCOPE SYSTEM HAVING ULTRASONIC MODULE

(71) Applicant: OLYMPUS CORPORATION, Tokyo (JP)

(72) Inventor: Junya Yamada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 14/738,334

(22) Filed: Jun. 12, 2015

(65) Prior Publication Data
US 2015/0279764 A1    Oct. 1, 2015

(30) Foreign Application Priority Data

Dec. 12, 2012  (JP) ................. 2012-271703

(51) Int. Cl.
*H01L 23/498*   (2006.01)
*A61B 8/12*   (2006.01)
(Continued)

(52) U.S. Cl.
CPC ............ *H01L 23/4985* (2013.01); *A61B 8/12* (2013.01); *A61B 8/445* (2013.01); *A61B 8/4483* (2013.01);
(Continued)

(58) Field of Classification Search
None
See application file for complete search history.

(56) References Cited

U.S. PATENT DOCUMENTS 4,385,255 A * 5/1983 Yamaguchi ........... B06B 1/0622
29/25.35
5,640,370 A   6/1997 Hanafy et al.
(Continued)

FOREIGN PATENT DOCUMENTS

CN    101356644 A     1/2009
EP    1 120 169 A1    8/2001
(Continued)

OTHER PUBLICATIONS

International Search Report dated Mar. 4, 2014 issued in PCT/JP2013/082506.
(Continued)

*Primary Examiner* — Michael Lebentritt
*Assistant Examiner* — Jordan Klein
(74) *Attorney, Agent, or Firm* — Scully, Scott, Murphy & Presser, P.C.

(57) ABSTRACT

A semiconductor device connection structure includes: a semiconductor element having a plate shape and including an external connection electrode on a surface of the semiconductor element; a support member which is stacked on the semiconductor element to be adhered to the semiconductor element and of which adhesion surface has a column shape that is substantially same as that of the semiconductor element, a thickness of the support member in a stacking direction being larger than that of the semiconductor element; and a flexible board configured to be electrically connected to the external connection electrode. The flexible board is arranged on a side surface of the semiconductor element and on a side surface of the support member and is adhered only to the side surface of the support member with an adhesive.

11 Claims, 11 Drawing Sheets

(51) Int. Cl.
  *A61B 8/00* (2006.01)
  *B06B 1/06* (2006.01)
(52) U.S. Cl.
  CPC .......... *A61B 8/4494* (2013.01); *B06B 1/0622* (2013.01); *H01L 23/498* (2013.01); *H01L 23/49838* (2013.01); *H01L 2924/0002* (2013.01)

(56) References Cited

U.S. PATENT DOCUMENTS

| | | | | |
|---|---|---|---|---|
| 5,810,009 | A * | 9/1998 | Mine | B06B 1/0622 310/334 |
| 8,198,787 | B2 | 6/2012 | Nakayama | |
| 8,294,817 | B2 | 10/2012 | Motohara et al. | |
| 8,872,412 | B2 | 10/2014 | Tezuka et al. | |
| 2001/0021809 | A1* | 9/2001 | De Jong | B06B 1/0614 600/458 |
| 2004/0002656 | A1* | 1/2004 | Sheljaskow | B06B 1/0622 600/459 |
| 2005/0225210 | A1 | 10/2005 | Englund et al. | |
| 2006/0238067 | A1 | 10/2006 | Dausch | |
| 2007/0073154 | A1* | 3/2007 | Karasawa | A61B 8/12 600/459 |
| 2007/0187844 | A1* | 8/2007 | Chen | H01L 23/041 257/789 |
| 2010/0013358 | A1* | 1/2010 | Nakayama | B06B 1/0633 310/348 |
| 2011/0218441 | A1* | 9/2011 | Osawa | A61B 8/14 600/445 |
| 2011/0248603 | A1* | 10/2011 | Tezuka | A61B 8/4405 310/314 |
| 2014/0116139 | A1* | 5/2014 | Endo | B06B 1/0622 73/584 |
| 2016/0372848 | A1* | 12/2016 | Yamada | H01R 9/0515 |

FOREIGN PATENT DOCUMENTS

| | | | |
|---|---|---|---|
| JP | H08-079894 A | 3/1996 | |
| JP | 10201759 A * | 8/1998 | ............. A61B 8/00 |
| JP | H10-201759 A | 8/1998 | |
| JP | 2004-363746 A | 12/2004 | |
| JP | 2008-028462 A | 2/2008 | |
| JP | 4100965 B2 | 6/2008 | |
| JP | 2008-535643 A | 9/2008 | |
| JP | 2009-188802 A | 8/2009 | |
| JP | 2010-022931 A | 2/2010 | |
| JP | 2011-223468 A | 11/2011 | |
| WO | 2007/095100 A2 | 8/2007 | |

OTHER PUBLICATIONS

Japanese Office Action dated Nov. 8, 2016 in related Japanese Patent Application No. 2012-271703.
Extended Supplementary European Search Report dated Jul. 5, 2016 in related European Application No. 13 86 1652.9.

* cited by examiner

SEMICONDUCTOR DEVICE CONNECTION STRUCTURE, ULTRASONIC MODULE, AND ULTRASONIC ENDOSCOPE SYSTEM HAVING ULTRASONIC MODULE

CROSS-REFERENCE TO RELATED APPLICATIONS

This application is a continuation of PCT international application Ser. No. PCT/JP2013/082506 filed on Dec. 3, 2013 which designates the United States, incorporated herein by reference, and which claims the benefit of priority from Japanese Patent Application No. 2012-271703, filed on Dec. 12, 2012, incorporated herein by reference.

BACKGROUND

1. Technical Field

The disclosure relates to a semiconductor device connection structure for connecting a semiconductor element and a flexible board, an ultrasonic module, and an ultrasonic endoscope system having the ultrasonic module.

2. Related Art

In the related art, there is disclosed a technique of adhering a base film in a side surface of a substrate with adhesive in a semiconductor device where a flexible board having inner leads and the base film is connected to the substrate having external connection electrodes (for example, refer to Japanese Patent No. 4100965).

There is disclosed a technique of fixing an imaging element to a flexible board with a guide member having a portion extending along a rear surface of the imaging element in an imaging module including the imaging element and the flexible board (for example, refer to Japanese Laid-open Patent Publication No. 2009-188802).

SUMMARY

In accordance with some embodiments, a semiconductor device connection structure, an ultrasonic module, and an ultrasonic endoscope system having the ultrasonic module are presented.

In some embodiments, a semiconductor device connection structure includes: a semiconductor element having a plate shape and including an external connection electrode on a surface of the semiconductor element; a support member which is stacked on the semiconductor element to be adhered to the semiconductor element and of which adhesion surface has a column shape that is substantially same as that of the semiconductor element, a thickness of the support member in a stacking direction being larger than that of the semiconductor element; and a flexible board configured to be electrically connected to the external connection electrode. The flexible board is arranged on a side surface of the semiconductor element and on a side surface of the support member and is adhered only to the side surface of the support member with an adhesive.

In some embodiments. an ultrasonic module includes: a plurality of ultrasonic transducers, each of which has a prismatic column shape and includes an external connection electrode on a surface thereof, the plurality of ultrasonic transducers being arranged in a direction perpendicular to a longitudinal direction of each of the plurality of ultrasonic transducers; a support member which is stacked on the plurality of ultrasonic transducers to be adhered to the plurality of ultrasonic transducers, a thickness of the support member in a stacking direction being larger than that of each of the plurality of ultrasonic transducers; and a flexible board configured to be connected to the external connection electrode. The flexible board is arranged on a side surface of each of the plurality of ultrasonic transducers and on a side surface of the support member and is adhered to the support member with an adhesive.

In some embodiments, an ultrasonic endoscope system having the above-described ultrasonic module.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the invention (hereinafter, referred to as "embodiments") will be described below with reference to the attached drawings. The present invention is not limited to the embodiments. The same reference signs are used to designate the same elements throughout the drawings. It is noted that the drawings are schematically illustrated and relationships between a thickness and a width of each member, ratios of each member, and the like are different from those of real members. There may be a portion of which dimension relation and ratio are different between figures of the drawings.

First Embodiment

Figure 1:
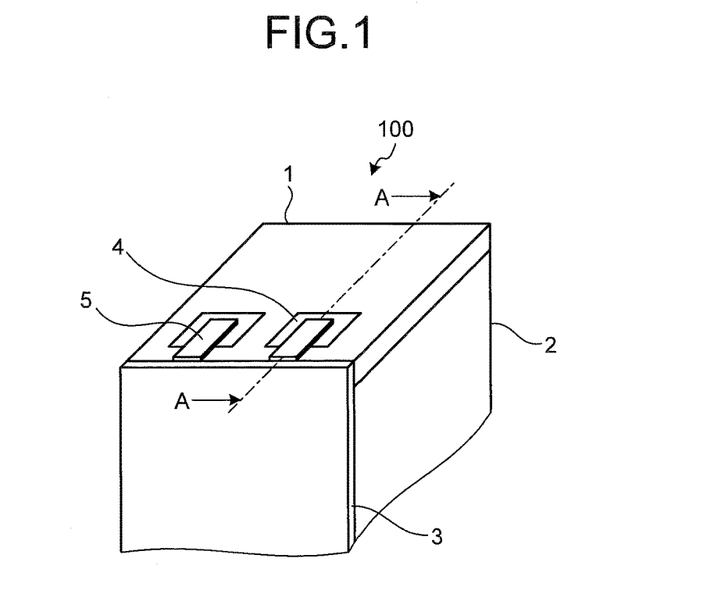
FIG. 1 is a perspective diagram illustrating a semiconductor device connection structure according to a first embodiment of the present invention.
Figure 2:
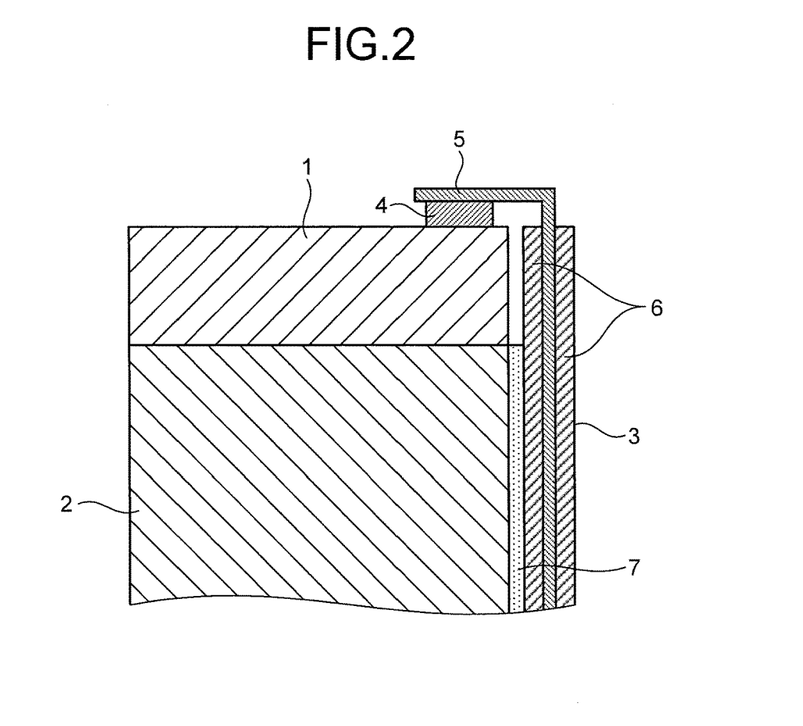
FIG. 2 is a cross-sectional diagram illustrating the semiconductor device connection structure taken along line A-A of FIG. 1.

FIG. 1 is a perspective diagram illustrating a semiconductor device connection structure according to a first embodiment of the present invention. FIG. 2 is a cross-sectional diagram illustrating the semiconductor device connection structure taken along line A-A of FIG. 1. A semiconductor device connection structure 100 according to the first embodiment of the present invention is configured to include a silicon substrate 1, a support member 2, and a flexible board 3.

The silicon substrate 1 has a plate shape and includes external connection electrodes 4 on a surface thereof. Although the silicon substrate 1 including the two external connection electrodes 4 is illustrated in FIG. 1, the number of external connection electrodes 4 is not limited thereto. The silicon substrate 1 is included in a semiconductor element of the present invention.

The support member 2 is stacked on the silicon substrate 1 to be adhered to the silicon substrate 1, and an adhesion surface of the support member 2 with respect to the silicon substrate 1 has the same columnar shape as that of the adhesion surface of the silicon substrate 1. In the first embodiment, a thickness of the support member 2 in the stacking direction is formed to be larger than a thickness of the silicon substrate 1 in the stacking direction. The thickness of the support member 2 is preferably about 0.5 mm or more.

The support member 2 is made of, for example, a resin or the like. The support member 2 processed in a specified shape is stacked on and adhered to the silicon substrate 1 by an adhesive. Otherwise, when the support member 2 is formed by curing an uncured resin, the support member may be adhered to the silicon substrate 1. The material of the support member 2 is not limited to a resin as long as the material ensures insulation.

The flexible board 3 has inner leads 5 inside thereof, and the inner leads 5 are covered with bendable insulating films 6. The flexible board 3 is disposed on a side surface of the silicon substrate 1 and a side surface of the support member 2, and by bending the inner leads 5 which are not covered with the insulating films 6, the flexible board 3 is connected to the external connection electrodes 4 of the silicon substrate 1. The inner leads 5 and the external connection electrodes 4 are electrically connected to each other, for example, by a conductive bonding material such as solder.

The support member 2 and the flexible board 3 are adhered to each other by an adhesive 7. In the first embodiment, since a thickness of the support member 2 in the stacking direction is formed to be larger than a thickness of the silicon substrate 1 in the stacking direction, an adhesion area is increased, so that it is possible to improve fixation strength.

In addition, in the first embodiment, since the side surface of the silicon substrate 1 and the flexible board 3 are not adhered to each other, the adhesive 7 is not infiltrated into the surface of the silicon substrate 1, and the performance of the silicon substrate 1 is not influenced.

In the semiconductor device connection structure 100 according to the first embodiment, the flexible board 3 is disposed on one side surface of the silicon substrate 1 to be connected thereto. However, individual flexible boards 3 may be disposed on the two side surfaces facing each other to be connected thereto.

Figure 3:
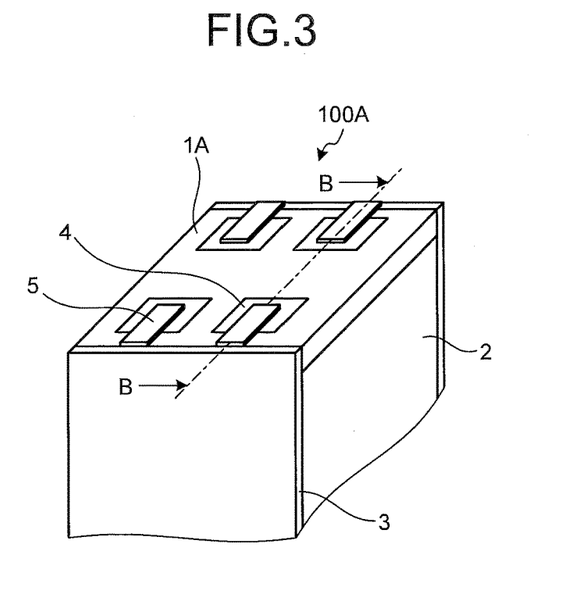
FIG. 3 is a perspective diagram illustrating a semiconductor device connection structure according to Modified Example 1 of the first embodiment of the present invention.
Figure 4:
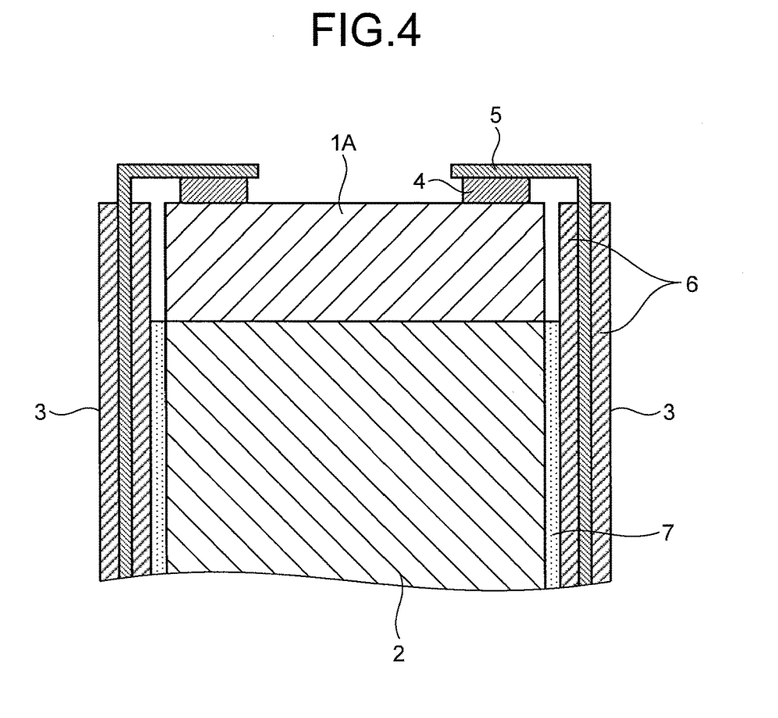
FIG. 4 is a cross-sectional diagram illustrating the semiconductor device connection structure taken along line B-B of FIG. 3.

FIG. 3 is a perspective diagram illustrating a semiconductor device connection structure according to Modified Example 1 of the first embodiment of the present invention. FIG. 4 is a cross-sectional diagram illustrating the semiconductor device connection structure taken along line B-B of FIG. 3. In a semiconductor device connection structure 100A according to Modified Example 1, individual flexible boards 3 are arranged on side surfaces of a silicon substrate 1A which face each other, and each flexible board 3 is adhered to a side surface of a support member 2 stacked on and adhered to the silicon substrate 1A, with an adhesive 7.

Similarly to the first embodiment, in Modified Example 1 according to the first embodiment, the thickness of the support member 2 in the stacking direction is formed to be larger than the thickness of the silicon substrate 1A in the stacking direction, and thus, the adhesion area is increased, so that it is possible to improve the fixation strength. In addition, similarly to the first embodiment, in Modified Example 1, since the adhesive 7 is not infiltrated into the surface of the silicon substrate 1A, it is possible to obtain the effect in that the performance of the silicon substrate 1A is not influenced.

Figure 5:
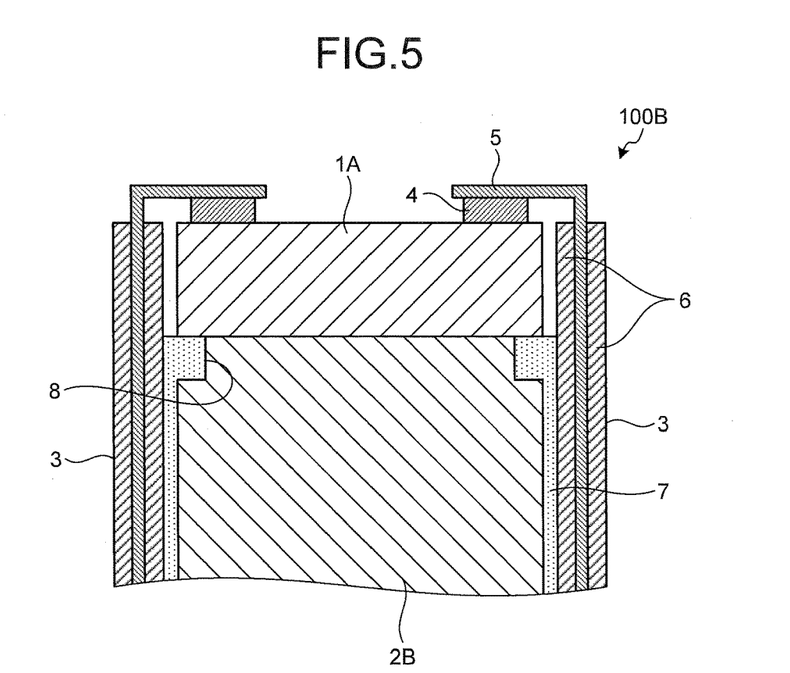
FIG. 5 is a cross-sectional diagram illustrating a semiconductor device connection structure according to Modified Example 2 of the first embodiment of the present invention.

In order to prevent the adhesive from being infiltrated into the silicon substrate, an adhesive reservoir portion may be formed in the support member. FIG. 5 is a cross-sectional diagram illustrating a semiconductor device connection structure according to Modified Example 2 of the first embodiment of the present invention. In a semiconductor device connection structure 100B according to Modified Example 2, trench-shaped adhesive reservoir portions 8 are formed in a support member 2B on the side of a contact surface of the support member 2B with respect to the silicon substrate 1A.

According to Modified Example 2 of the first embodiment, the thickness of the support member 2B in the stacking direction is formed to be larger than the thickness of the silicon substrate 1A in the stacking direction, and thus, the adhesion area is increased, thereby improving the fixation strength. Further, since the adhesive reservoir portions 8 are provided, it is possible to effectively suppress the infiltration of the adhesive 7 into the surface of the silicon substrate 1, so that the performance of the silicon substrate 1A is not influenced.

Figure 6:
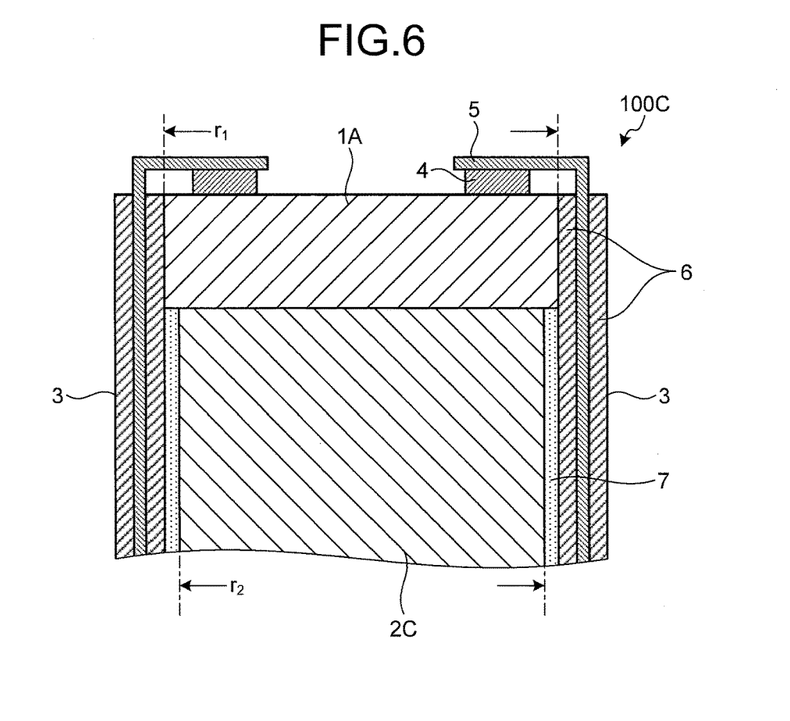
FIG. 6 is a cross-sectional diagram illustrating a semiconductor device connection structure according to Modified Example 3 of the first embodiment of the present invention.

Furthermore, in order to prevent the adhesive from being infiltrated into the silicon substrate 1A, the support member 2B is formed to be smaller than the silicon substrate 1A. For example, a length of a side of an adhesion surface of the support member 2B with respect to the silicon substrate 1A, which is not in contact with the flexible board 3, is formed to smaller than that of the silicon substrate 1A. FIG. 6 is a cross-sectional diagram illustrating a semiconductor device connection structure according to Modified Example 3 of the first embodiment of the present invention. In Modified Example 3 of the first embodiment, a length $r_2$ of a side of an adhesion surface of a support member 2C with respect to the silicon substrate 1A, which is not contact with the flexible board 3, is formed to be smaller than a length $r_1$ of a side of the silicon substrate 1A which is not in contact with the flexible board 3.

According to Modified Example 3 of the first embodiment, the thickness of the support member 2C in the stacking direction is formed to be larger than the thickness of the silicon substrate 1A in the stacking direction, and thus, the adhesion area is increased, thereby improving the fixation strength. In addition, the length $r_2$ of the side of the adhesion surface of the support member 2C with respect to the silicon substrate 1A, which is not in contact with the flexible board 3, is formed to be smaller than the length $r_1$ of the side of the silicon substrate 1A which is not in contact with the flexible board 3, and thus, the gap between the silicon substrate 1A and the flexible board 3 becomes small, so that it is possible to effectively suppress the infiltration of the adhesive 7 into the surface of the silicon substrate 1A, and the performance of the silicon substrate 1A is not influenced. Although there is no gap between the silicon substrate 1A and the flexible board 3 in FIG. 6, there may be a gap between the silicon substrate 1A and the flexible board 3.

Second Embodiment

Figure 7:
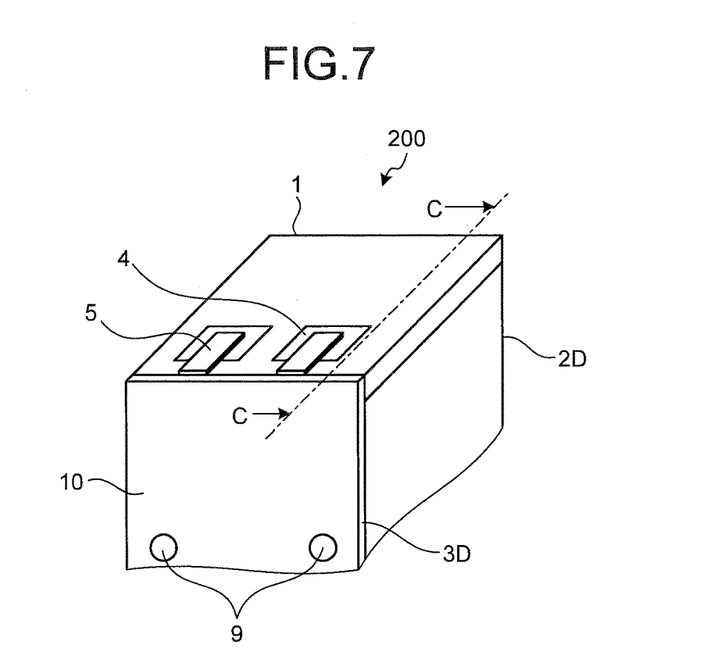
FIG. 7 is a perspective diagram illustrating a semiconductor device connection structure according to a second embodiment of the present invention.
Figure 8:
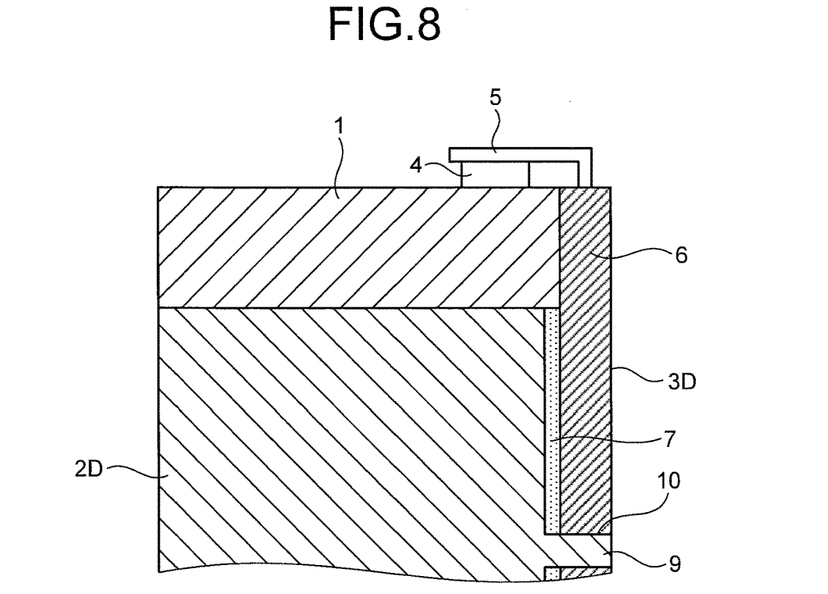
FIG. 8 is a cross-sectional diagram illustrating the semiconductor device connection structure taken along line C-C of FIG. 7.

FIG. 7 is a perspective diagram illustrating a semiconductor device connection structure according to a second embodiment of the present invention. FIG. 8 is a cross-sectional diagram illustrating the semiconductor device connection structure taken along line C-C of FIG. 7. A semiconductor device connection structure 200 according to the second embodiment is different from that of the first embodiment in that alignment marks for aligning a flexible board 3D are formed in a support member 2D.

Alignment protrusions 9 as alignment marks are formed in the support member 2D. In the flexible board 3D, alignment holes 10 which are fitted into the alignment protrusions 9 are formed.

According to the second embodiment, the thickness of the support member 2D is formed to be larger than the thickness of the silicon substrate 1, and thus, the adhesion area is increased, so that it is possible to improve the fixation strength. In addition, since the side surface of the silicon substrate 1 and the flexible board 3D are not adhered to each other, the adhesive 7 is not infiltrated into the surface of the silicon substrate 1, and the performance of the silicon substrate 1 is not influenced. In addition, the alignment protrusions 9 and the alignment holes 10 are aligned to be fitted to each other, so that it is possible to simply perform alignment and to easily perform connection. Although there is no gap between the silicon substrate 1 and the flexible board 3D in FIG. 8, there may be a gap between the silicon substrate 1 and the flexible board 3D.

Third Embodiment

Figure 9:
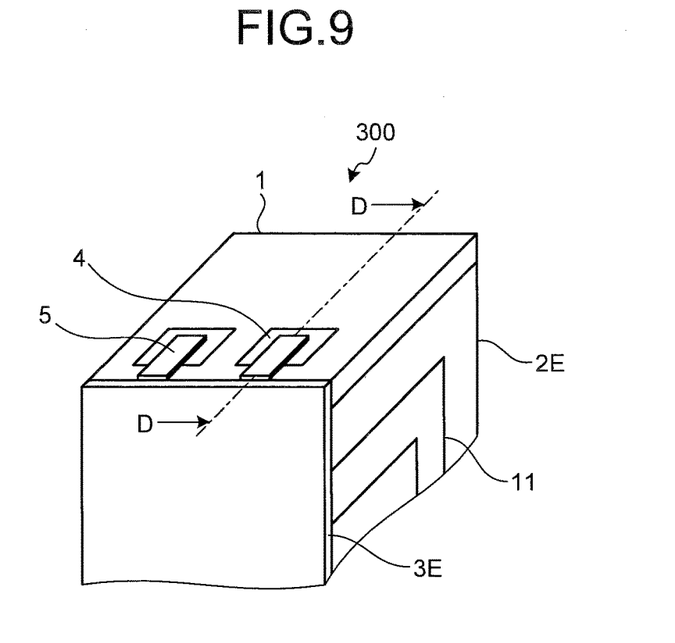
FIG. 9 is a perspective diagram illustrating a semiconductor device connection structure according to a third embodiment of the present invention.
Figure 10:
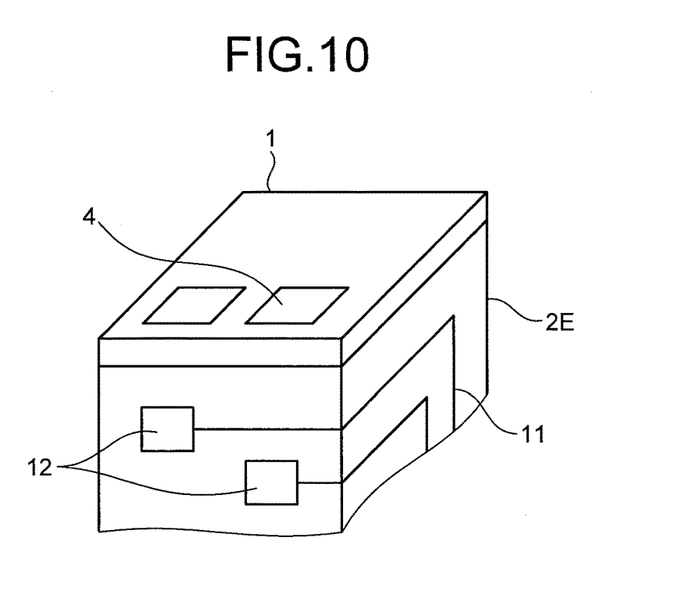
FIG. 10 is a perspective diagram illustrating a structure before adhesion of a flexible board of the semiconductor device connection structure according to the third embodiment of the present invention.
Figure 11:
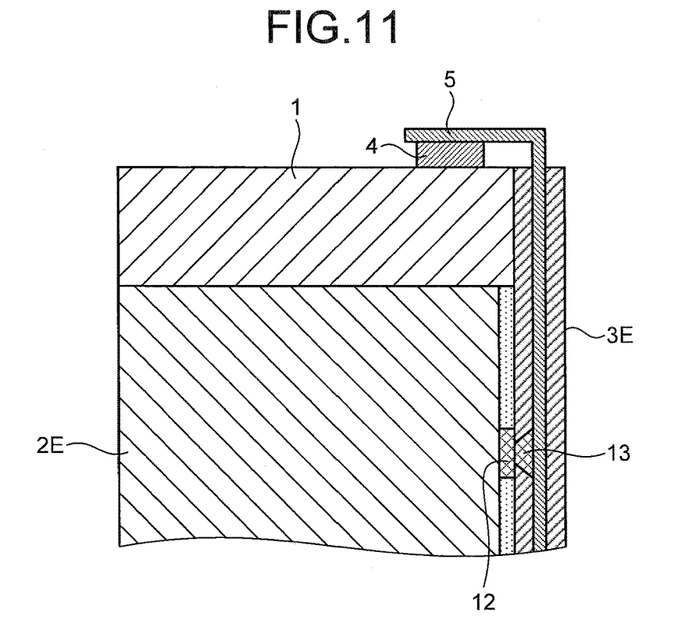
FIG. 11 is a cross-sectional diagram illustrating the semiconductor device connection structure taken along line D-D of FIG. 9.

FIG. 9 is a perspective diagram illustrating a semiconductor device connection structure according to a third embodiment of the present invention. FIG. 10 is a perspective diagram illustrating a structure before adhesion of a flexible board of the semiconductor device connection structure according to the third embodiment of the present invention. FIG. 11 is a cross-sectional diagram illustrating the semiconductor device connection structure taken along line D-D of FIG. 9. A semiconductor device connection structure 300 according to the third embodiment is different from that of the first and second embodiments in that a circuit is formed on a support member 2E.

As illustrated in FIGS. 9 and 10, a circuit such as wire lines 11 and connection electrodes 12 are formed on the support member 2E. The support member 2E may be manufactured with a silicon substrate where a circuit is formed, an MID (Molded Interconnect Device) where a circuit is formed on a resin, a glass epoxy substrate or a ceramic substrate where a circuit is formed, or the like.

As illustrated in FIG. 11, the connection electrode 12 is connected to a connection electrode 13 formed in a flexible board 3E.

According to the third embodiment, the thickness of the support member 2E is formed to be larger than the thickness of the silicon substrate 1, and thus, the adhesion area is increased, so that it is possible to improve the fixation strength. In addition, since the side surface of the silicon substrate 1 and the flexible board 3E are not adhered to each other, the adhesive 7 is not infiltrated into the surface of the silicon substrate 1, and the performance of the silicon substrate 1 is not influenced. In addition, since a circuit is formed on the support member 2E, a degree of freedom of wiring routing is high. In addition, since an electronic component can be mounted on the support member 2E, the space can be effectively used, and thus, the size can also be reduced. Although there is no gap between the silicon substrate 1 and the flexible board 3E in FIG. 11, there may be a gap between the silicon substrate 1 and the flexible board 3E.

Figure 12:
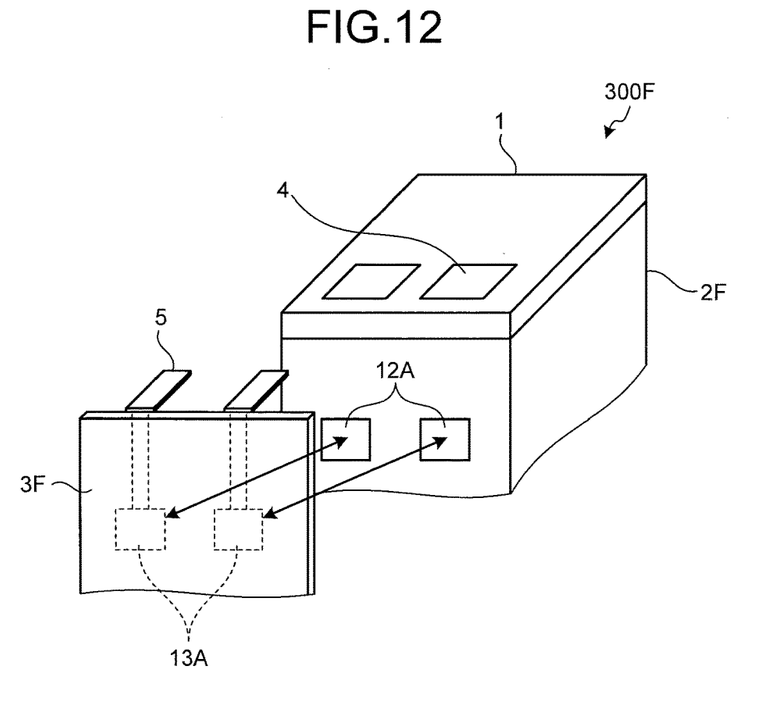
FIG. 12 is a perspective diagram illustrating a semiconductor device connection structure according to Modified Example of the third embodiment of the present invention.

As illustrated in FIG. 12, as alignment marks, alignment electrodes 12A are formed on a support member 2F, and alignment electrodes 13A are formed on a flexible board 3F, alignment is easily performed, so that it is possible to simply manufacture a semiconductor device connection structure 300F.

Fourth Embodiment

Figure 13:
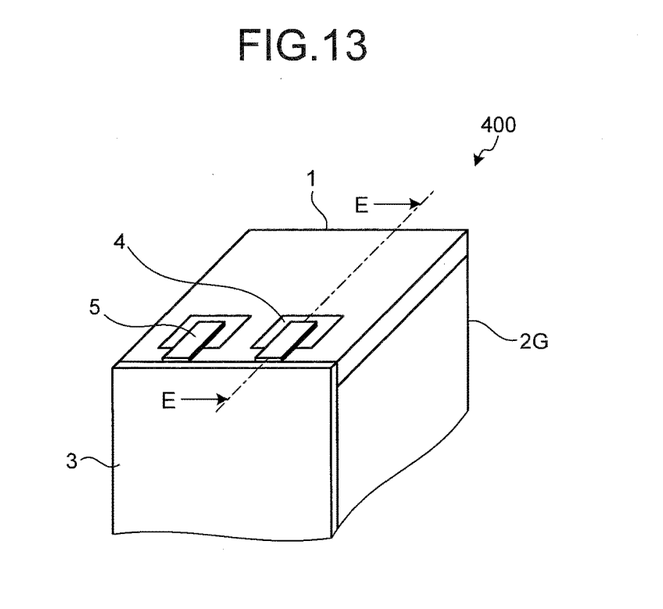
FIG. 13 is a perspective diagram illustrating a semiconductor device connection structure according to a fourth embodiment of the present invention.
Figure 14:
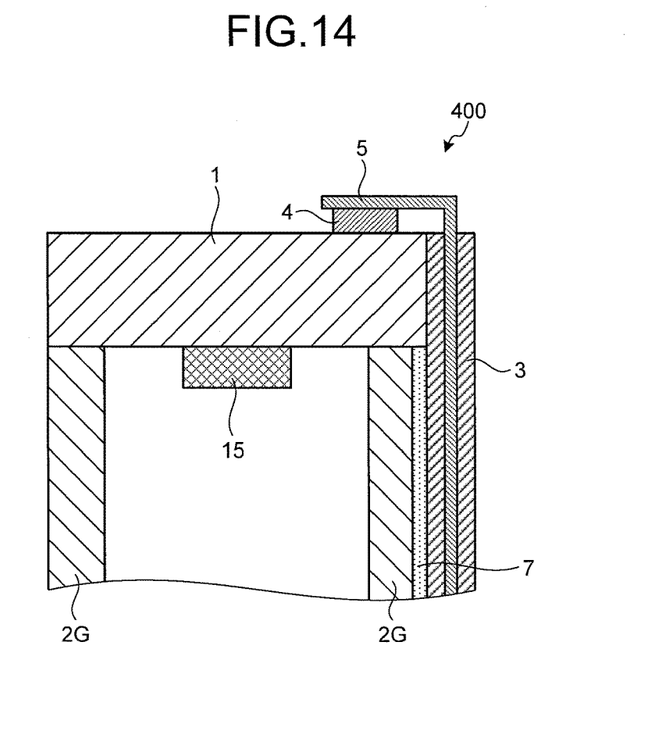
FIG. 14 is a cross-sectional diagram illustrating the semiconductor device connection structure taken along line E-E of FIG. 13.

FIG. 13 is a perspective diagram illustrating a semiconductor device connection structure according to a fourth embodiment of the present invention. FIG. 14 is a cross-sectional diagram illustrating the semiconductor device connection structure taken along line E-E of FIG. 13. A semiconductor device connection structure 400 according to the embodiment is different from that of the first embodiment in that a support member 2G is hollow inside.

In the semiconductor device connection structure 400, the support member 2G is hollow inside, so that an electronic component 15 and the like can be mounted in the space.

According to the fourth embodiment, the thickness of the support member 2G is formed to be larger than the thickness of the silicon substrate 1, and thus, the adhesion area is increased, so that it is possible to improve the fixation strength. In addition, since the side surface of the silicon substrate 1 and the flexible board 3 are not adhered to each other, the adhesive 7 is not infiltrated into the surface of the silicon substrate 1, and the performance of the silicon substrate 1 is not influenced. In addition, since the support member 2G is formed to be hollow inside, the electronic component 15 can be mounted, so that it is possible to effectively use the space, and thus, the size can also be reduced.

Figure 15:
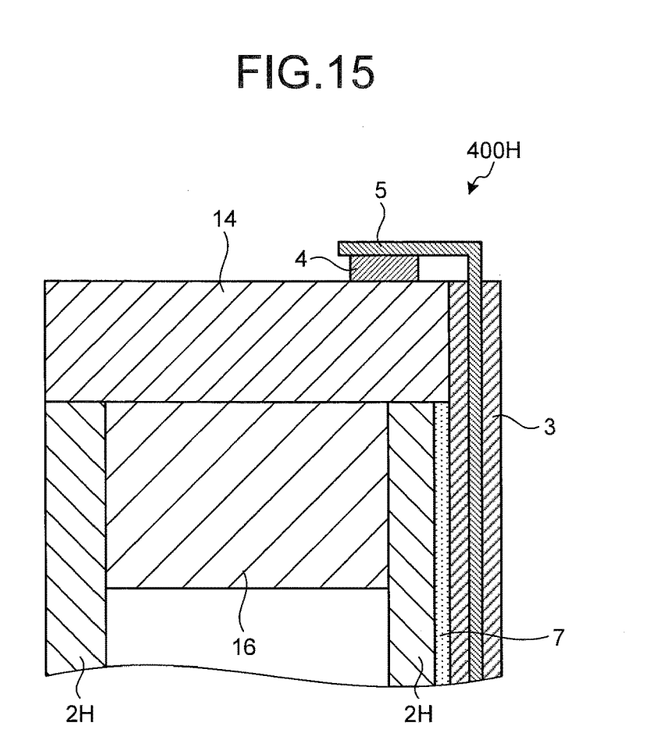
FIG. 15 is a cross-sectional diagram illustrating a semiconductor device connection structure according to Modified Example of the fourth embodiment of the present invention.

In the case where an ultrasonic transducer is used as a semiconductor device, a backing material can be disposed in the hollow portion inside the support member. FIG. 15 is a cross-sectional diagram illustrating a semiconductor device connection structure according to Modified Example 1 of the fourth embodiment of the present invention. Here, a backing material 16 is disposed just on the inner surface of an ultrasonic vibration generating portion of the ultrasonic transducer 14.

In a semiconductor device connection structure 400H according to Modified Example 1, a support member 2H supporting the ultrasonic transducer 14 is formed to be hollow inside, and the backing material 16 is disposed in the space, so that necessary vibration attenuation can be secured, and ultrasonic characteristics can be improved. Therefore, it is possible to realize a high image quality of an ultrasonic image.

Furthermore, according to Modified Example 1, the thickness of the support member 2H is formed to be larger than the thickness of the ultrasonic transducer 14, and thus, the adhesion area is increased, so that it is possible to improve the fixation strength. In addition, since the side surface of the ultrasonic transducer 14 and the flexible board 3 are not adhered to each other, mechanical deformation of the ultrasonic transducer 14 is not obstructed.

Fifth Embodiment

Figure 16:
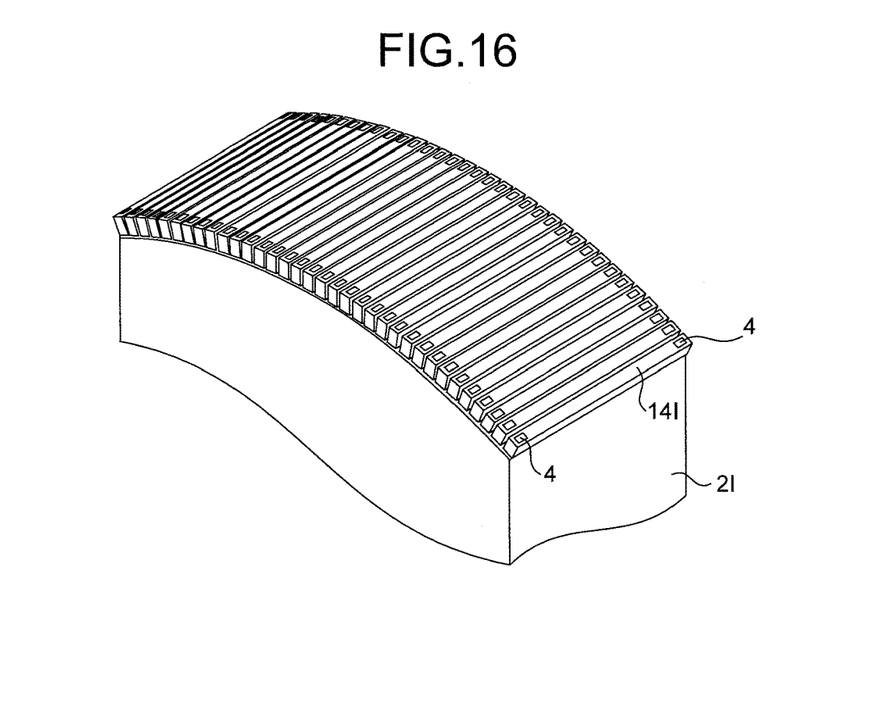
FIG. 16 is a schematic diagram illustrating a configuration of an ultrasonic transducer used for an ultrasonic module according to a fifth embodiment of the present invention.
Figure 17:
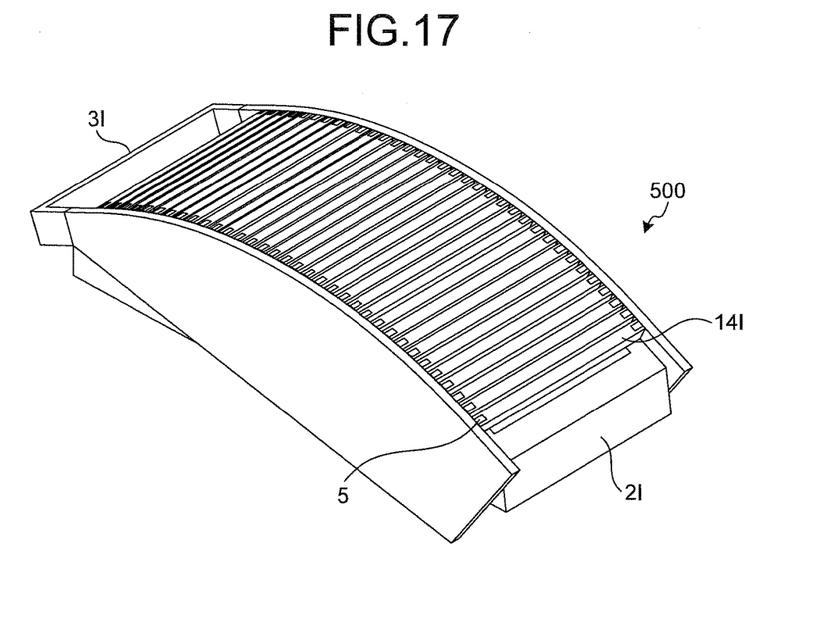
FIG. 17 is a schematic perspective diagram illustrating the ultrasonic module according to the fifth embodiment of the present invention.

FIG. 16 is a schematic diagram illustrating a configuration of an ultrasonic transducer used for an ultrasonic module according to a fifth embodiment of the present invention. FIG. 17 is a schematic perspective diagram illustrating the ultrasonic module according to the fifth embodiment of the present invention. In FIG. 17, only the connection structure portion of an ultrasonic module 500 is illustrated, and the lower portion of the ultrasonic module 500 is omitted in illustration.

As illustrated in FIGS. 16 and 17, in the ultrasonic module 500 according to the fifth embodiment, ultrasonic transducers 14I have a prismatic column shape, and the plurality of ultrasonic transducers 14I are arranged in the direction perpendicular to the longitudinal direction to be adhered to a support member 2I. The surface of the support member 2I to which the ultrasonic transducers 14I are adhered has a curved shape, so that the plurality of ultrasonic transducers 14I are arranged in a curved shape. Similarly to the support member 2H according to the fourth embodiment, preferably, the support member 2I is formed to be hollow inside, and a backing material is disposed in the hollow portion.

External connection electrodes 4 are formed on respective two ends of the ultrasonic transducer 14I, and the external connection electrodes 4 are connected to inner leads 5 in a flexible board 3I having a predetermined shape.

According to the fifth embodiment, the thickness of the support member 2I is formed to be larger than the thickness of the ultrasonic transducer 14I, and thus, the adhesion area is increased, so that it is possible to improve the fixation strength. In addition, since the side surface of the ultrasonic transducer 14I and the flexible board 3I are not adhered to each other, mechanical deformation of the ultrasonic transducer 14I is not obstructed. In addition, the plurality of ultrasonic transducers 14I having a prismatic column shape are arranged, so that it is possible to easily manufacture the ultrasonic module 500 having a desired shape.

Figure 18:
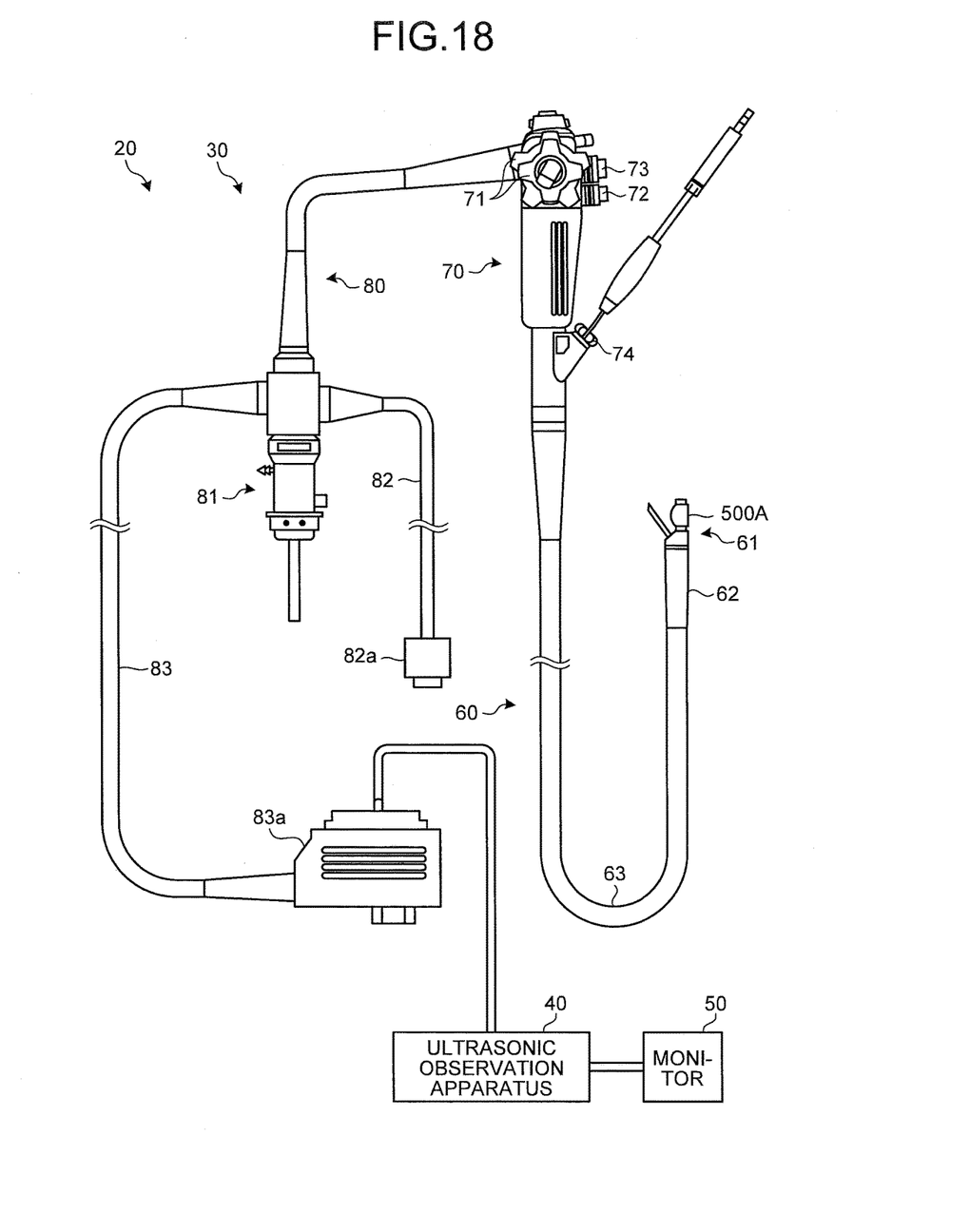
FIG. 18 is a diagram illustrating an overall configuration of an ultrasonic endoscope system using an ultrasonic module.
Figure 19:
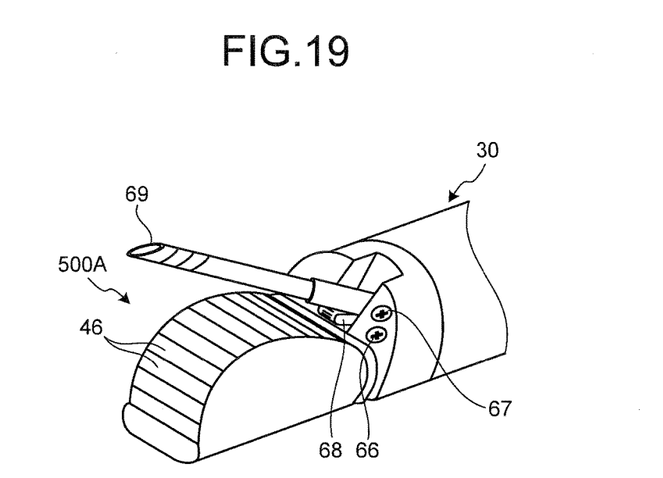
FIG. 19 is a diagram illustrating a structure of a distal end portion of an insertion portion of the ultrasonic endoscope system of FIG. 18.
Figure 20:
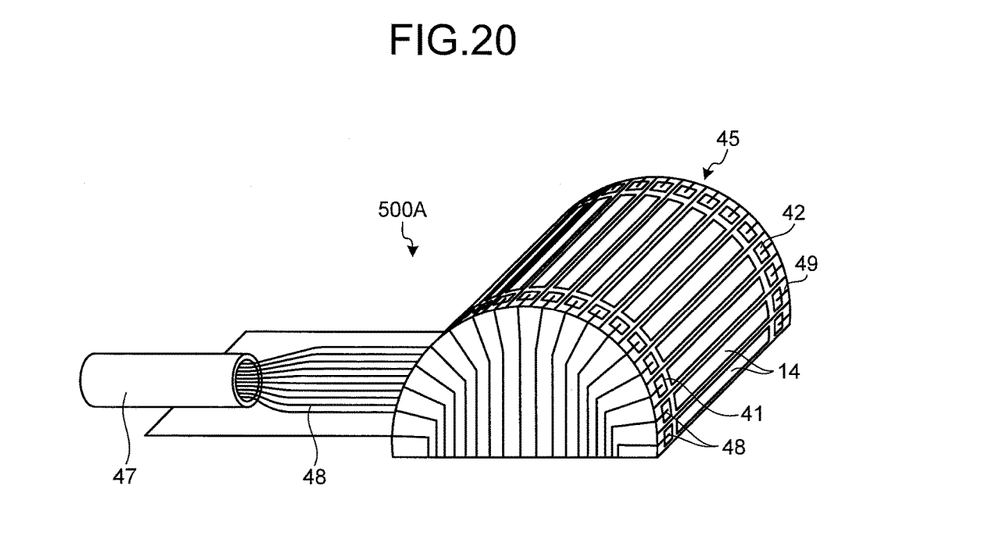
FIG. 20 is a diagram illustrating a structure of the ultrasonic module in the distal end portion of FIG. 19.

The above-described ultrasonic module 500 according to the fifth embodiment is, for example, provided at the distal end of an ultrasonic endoscope 30 of an ultrasonic endoscope system 20 illustrated in FIG. 18. FIG. 18 is a diagram illustrating an overall configuration of an ultrasonic endoscope system using an ultrasonic module. FIG. 19 is a diagram illustrating a structure of a distal end portion of an insertion portion of the ultrasonic endoscope system of FIG. 18. FIG. 20 is a diagram illustrating a structure of the ultrasonic module in the distal end portion of FIG. 19.

First, the overall configuration of the ultrasonic endoscope system 20 will be described. The ultrasonic endoscope system 20 illustrated in FIG. 18 is configured to include the ultrasonic endoscope 30, an ultrasonic observation apparatus 40, and a monitor 50. The ultrasonic endoscope 30 is configured to include a thin, long insertion portion 60 which is inserted into a body, an operating unit 70 which is continuously arranged in a proximal end of the insertion portion 60, and a universal cord 80 which is extended from a side portion of operating unit 70.

Herein, at a proximal end portion of the universal cord 80, a connector 81 to be connected to a light source device (not illustrated) is arranged. A cable 82 which is connected to a camera control unit (not illustrated) through a connector 82a and a cable 83 which is detachably connected to the ultrasonic observation apparatus 40 through a connector 83a are extended from the connector 81. The ultrasonic observation apparatus 40 is connected to the ultrasonic endoscope 30 through the connector 83a, and the monitor 50 is connected to the ultrasonic endoscope through the ultrasonic observation apparatus 40.

The insertion portion 60 is configured by continuously arranging, in order from the distal end side, a distal end rigid portion (hereinafter, referred to as a "distal end portion") 61, a bending portion 62 which is disposed at the rear stage of the distal end portion 61, and a thin, long flexible tube 63 which is disposed at the rear stage of the bending portion 62 and reaches the operating unit 70 as main components.

As illustrated in FIG. 19, an ultrasonic module 500A is arranged at the distal end side of the distal end portion 61. The ultrasonic module 500A is an ultrasonic module according to Modified Example of the fifth embodiment. At a side closer to a base portion than the ultrasonic module 500A, in the distal end portion 61, an illumination lens 66 constituting an illumination optical system and an observation lens 67 of an observation optical system are arranged, and a forceps opening 68 which is a distal end opening which is also used as a suction opening is an outlet of a treatment tool insertion channel. A treatment tool raising base (not illustrated) is arranged in the forceps opening 68. A manipulation wire (not illustrated) is connected to the treatment tool raising base, and by manipulating a forceps raising knob (not illustrated), the manipulation wire is drawn, so that an extraction angle of a puncture needle 69 extracted from the treatment tool insertion channel can be adjusted.

The operating unit 70 is provided with an angle knob 71 which controls a bending portion 62 to be bent to a desired direction, an air/water supply button 72 which performs air and water supply manipulations, a suction button 73 which performs a suction manipulation, and a treatment tool insertion opening 74 which is an entrance of the treatment tool configured to be introduced into a body.

The treatment tool insertion opening 74 communicates with the forceps opening 68 through a treatment tool insertion channel (not illustrated) provided inside the insertion portion 60. A sheath of the ultrasonic treatment tool (not illustrated) can be inserted into the treatment tool insertion opening 74. The puncture needle 69 inserted into the sheath is formed to protrude from the forceps opening 68, so that the puncture needle 69 can be arranged to be ejected and retreated within a field of view for observation of the ultrasonic module 500A.

As illustrated in FIG. 20, an ultrasonic transducer array 45 of the ultrasonic module 500A includes a plurality of ultrasonic transducer elements 46 having, for example, a rectangular shape in a plan view, and the ultrasonic transducer array is configured as a convex-type transducer group where the long sides of the ultrasonic transducer elements 46 are connected to each other to be arranged to be curved in an arc shape. That is, in the ultrasonic transducer array 45, for example, one hundred of the ultrasonic transducer elements 46 having a short side of 0.1 mm or less are arranged on a side surface having an arc with a radius of 5 mm in a 180-degree direction. Although the ultrasonic transducer array 45 illustrated in FIG. 20 is of convex type, for example, a radial-type vibrator group having a two-dimensional array a linear-type vibrator group which is not curved may be employed.

At the one end portion of the arc-shaped ultrasonic transducer array 45, electrode terminals 41 provided at the one end portions of the ultrasonic transducer elements 46 are arranged. The electrode terminals 41 are connected to signal lines 48 branched from a coaxial cable bundle 47 through the flexible board (FPC board). On the other hand, electrode terminals 42 provided at the other end portions of the ultrasonic transducer elements 46 are arranged at the other end portion of the ultrasonic transducer array 45, and the electrode terminals 42 are connected to a ground line 49 branched from the coaxial cable bundle 47.

In the ultrasonic endoscope system 20 configured as described above, the ultrasonic module 500A which performs transmission and reception of the ultrasonic wave is arranged at the distal end of the insertion portion 60, an ultrasonic image of an organ or the like obtained by inserting the insertion portion 60 into a body of a subject is displayed on the display unit of the monitor 50, and an in-vivo image captured by an endoscopic observation function is displayed on the display unit, so that it is possible to perform observation, diagnosis, and the like on a diagnosis subject.

According to some embodiments, because a flexible board arranged on side surfaces of a semiconductor element and a support member is adhered to the support member stacked on and adhered to the semiconductor element, it is possible to improve adhesion strength without influencing performance of the semiconductor element.

As described heretofore, a semiconductor device connection structure according to some embodiments is useful for a semiconductor device where various types of semiconductor elements are mounted, and particularly, the semiconductor device connection structure is suitable for an endoscope system having an ultrasonic probe for observing an inside of an organ of a subject or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A semiconductor device connection structure comprising:
   a semiconductor element having a plate shape and including an external connection electrode on a top surface of the semiconductor element;
   a support member having an adhesion surface on which the semiconductor element is stacked and adhered, with a rear surface of the semiconductor element being in contact with the adhesion surface, wherein the adhesion surface has a substantially same shape as the rear surface of the semiconductor element, and the support member having a column shape with a thickness in a stacking direction larger than a thickness of the semiconductor element in the stacking direction;
   a flexible board including an insulating film and an inner lead, the inner lead having a first portion and a second portion, the first portion being covered with the insulating film and the second portion being exposed from the insulating film, the second portion being bent so as to be connected to the external connection electrode on the top surface of the semiconductor element, and
   an adhesive arranged on a side surface of the support member, the flexible board being arranged on a side surface of the semiconductor element and on the side surface of the support member such that the flexible board being adhered only to the side surface of the support member with the adhesive.

2. The semiconductor device connection structure according to claim 1, further comprising an adhesive reservoir portion in the support member, the adhesive reservoir being positioned in a vicinity of an adhesion surface of the support member to the semiconductor element.

3. The semiconductor device connection structure according to claim 1, wherein the support member is arranged on the semiconductor element such that a gap between the side surface of the semiconductor element and the flexible board is narrower than a gap between the side surface of the support member and the flexible board.

4. The semiconductor device connection structure according to claim 1, further comprising one or more alignment marks in the support member and the flexible board.

5. The semiconductor device connection structure according to claim 1, further comprising a circuit on the support member.

6. The semiconductor device connection structure according to claim 4, wherein the one or more alignment marks are one or more electrodes.

7. The semiconductor device connection structure according to claim 1, wherein the support member includes a hollow portion.

8. The semiconductor device connection structure according to claim 7, wherein
   the semiconductor element is an ultrasonic transducer, and
   the semiconductor device connection structure further comprises a backing material disposed in the hollow portion in the support member and configured to absorb propagation of an ultrasonic wave.

9. The semiconductor device connection structure according to claim 7, further comprising an electronic component mounted on the support member in the hollow portion.

10. An ultrasonic module comprising:
a plurality of ultrasonic transducers, each of which has a prismatic column shape and includes an external connection electrode on a top surface thereof, the plurality of ultrasonic transducers being arranged in a direction perpendicular to a longitudinal direction of each of the plurality of ultrasonic transducers;
a support member having an adhesion surface on which the plurality of ultrasonic transducers are stacked and adhered, with a rear surface of the plurality of ultrasonic transducers being in contact with the adhesion surface, the support member having a column shape with a thickness in a stacking direction larger than a thickness of each of the plurality of ultrasonic transducers in the stacking direction;
a flexible board including an insulating film and an inner lead, the inner lead having a first portion and a second portion, the first portion being covered with the insulating film and the second portion being exposed from the insulating film, the second portion being bent so as to be connected to the external connection electrode on the top surface of the plurality of ultrasonic transducers, and
an adhesive arranged on a side surface of the support member, the flexible board being arranged on a side surface of each of the plurality of ultrasonic transducers and on the side surface of the support member such that the flexible board being only adhered to the support member with the adhesive.

11. An ultrasonic endoscope system having the ultrasonic module according to claim 10.

* * * * *

UNITED STATES PATENT AND TRADEMARK OFFICE
CERTIFICATE OF CORRECTION

PATENT NO. : 9,997,449 B2  
APPLICATION NO. : 14/738334  
DATED : June 12, 2018  
INVENTOR(S) : Junya Yamada It is certified that error appears in the above-identified patent and that said Letters Patent is hereby corrected as shown below:

On the Title Page

Item [63], insert:  
--Continuation of Application PCT/JP2013/082506, filed on Dec. 3, 2013--

Signed and Sealed this  
Eleventh Day of December, 2018

Andrei Iancu  
*Director of the United States Patent and Trademark Office*